United States Patent [19]

Webinger

[11] 4,277,014
[45] Jul. 7, 1981

[54] AIR FRESHENER

[75] Inventor: George Webinger, Minneapolis, Minn.

[73] Assignee: Champion International Corporation, Stamford, Conn.

[21] Appl. No.: 102,898

[22] Filed: Dec. 12, 1979

[51] Int. Cl.³ .......................... B65D 5/32; B65D 5/38
[52] U.S. Cl. .................................. 229/11; 229/23 BT; 229/41 C; 239/58
[58] Field of Search ................. 229/9, 10, 11, 19, 20, 229/23 BT, 41 C; 239/58, 59, 60

[56] References Cited

U.S. PATENT DOCUMENTS

| 2,307,076 | 1/1943 | Ray | 229/41 C |
|---|---|---|---|
| 2,683,953 | 7/1954 | Hopkins | 229/23 BT X |
| 2,832,466 | 4/1958 | Sheard | 229/41 C X |
| 3,261,533 | 7/1966 | Repking | 229/41 C X |
| 3,286,872 | 11/1966 | Burdick, Jr. | 239/58 X |
| 3,738,563 | 6/1973 | Eifrid | 229/23 BT |
| 3,877,631 | 4/1975 | Lai et al. | 228/23 BT X |
| 3,944,072 | 3/1976 | Budington | 229/41 C X |
| 3,973,724 | 8/1976 | Stone | 229/41 C X |

Primary Examiner—Davis T. Moorhead
Attorney, Agent, or Firm—Evelyn M. Sommer

[57] ABSTRACT

An air freshener carton includes a regular, polygonally-shaped lower unit and a complementally shaped upper unit which are movable relative to each other along a common, longitudinal axis. The upper unit has a plurality of openings spaced about its top wall which are selectively opened by relative movement of the units away from each to enable air to circulate through the openings to contact and diffuse an active air freshener material housed within the lower unit.

14 Claims, 14 Drawing Figures

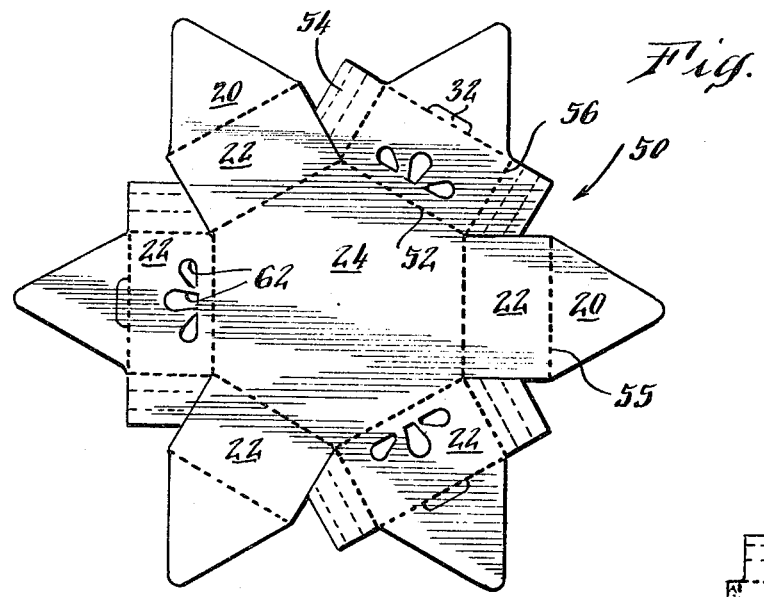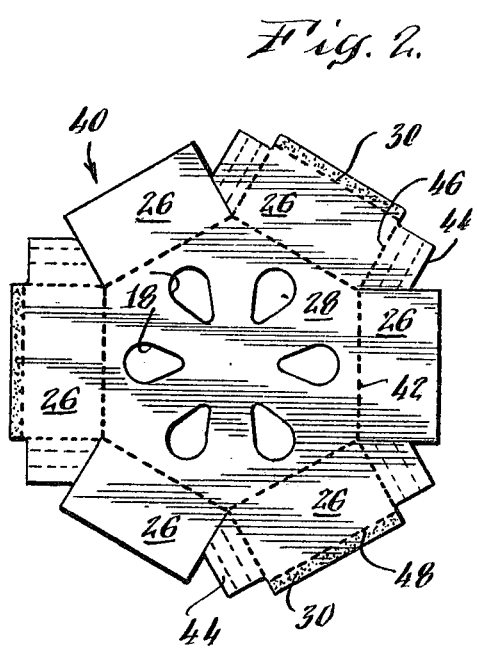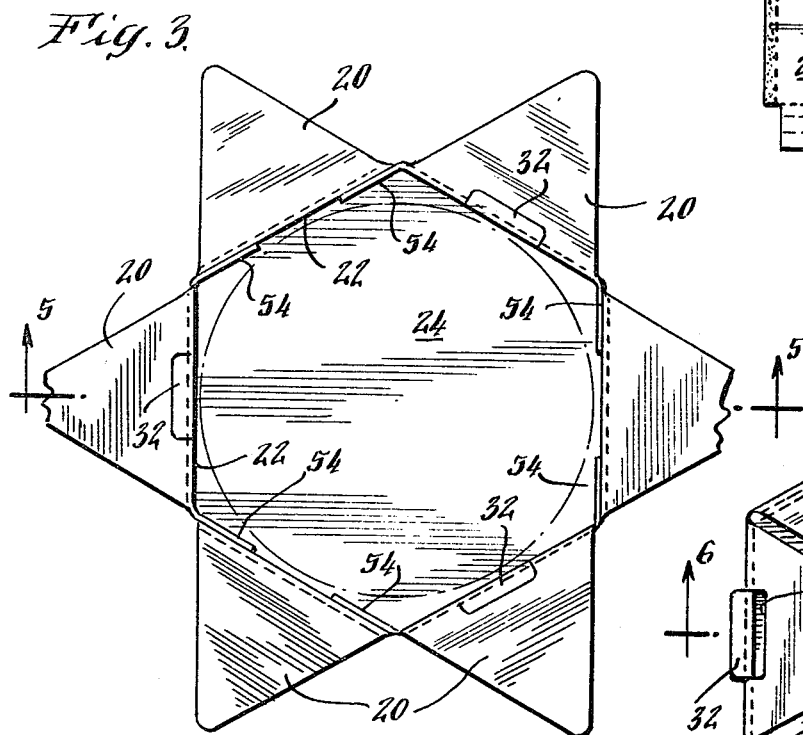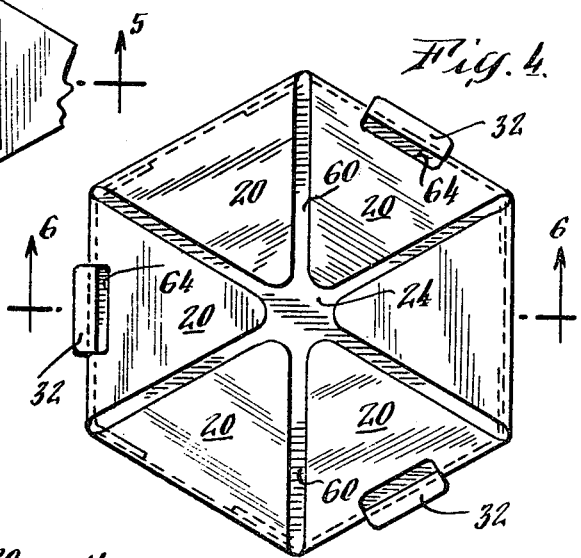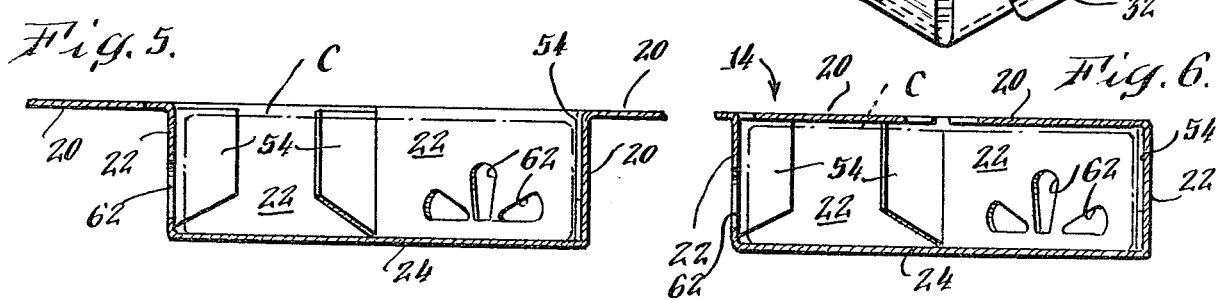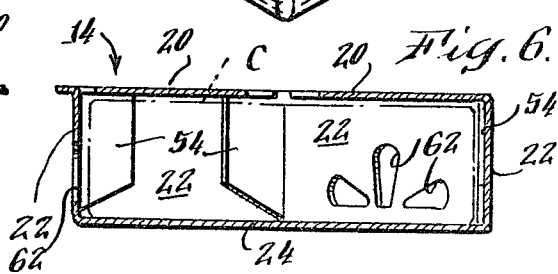

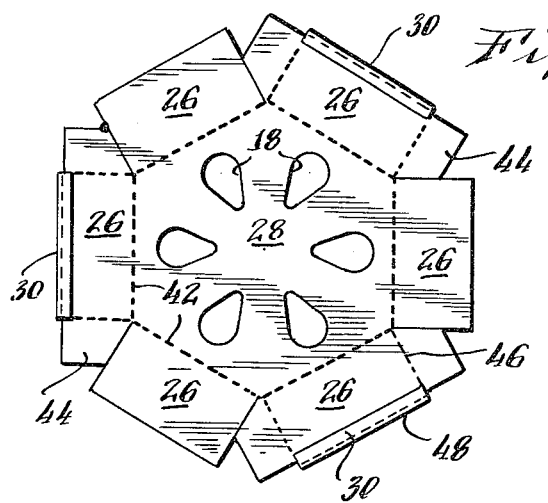
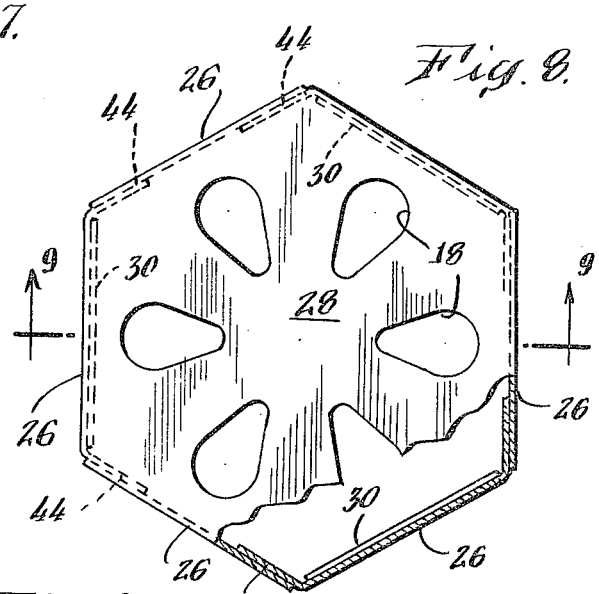
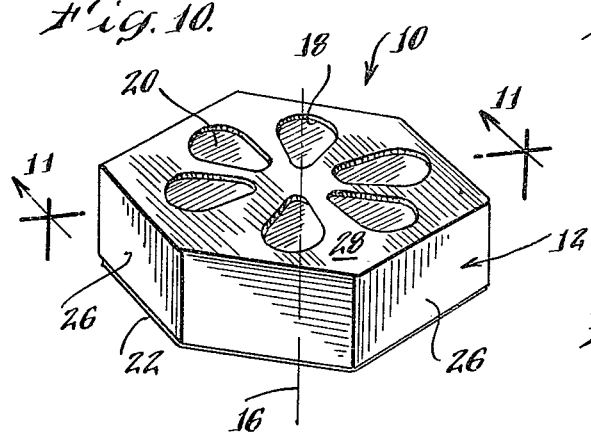
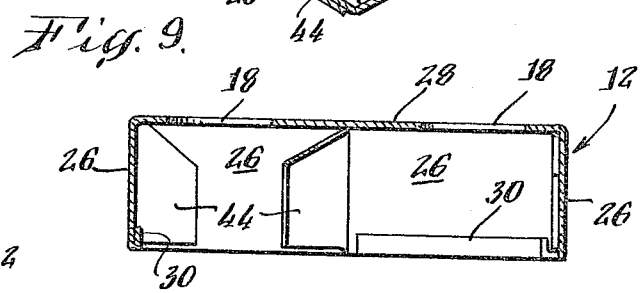
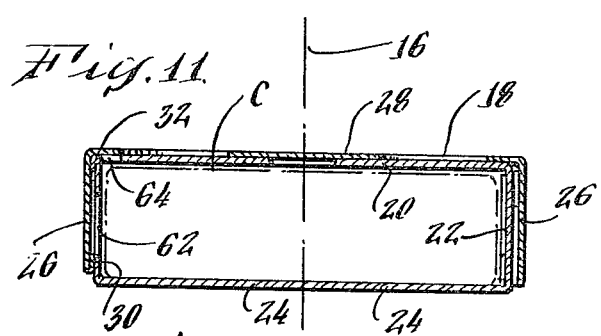
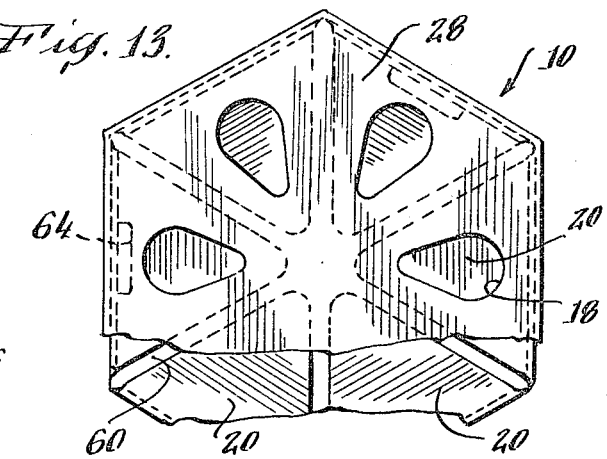
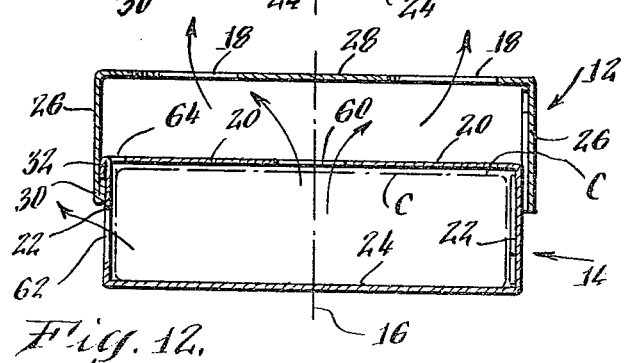
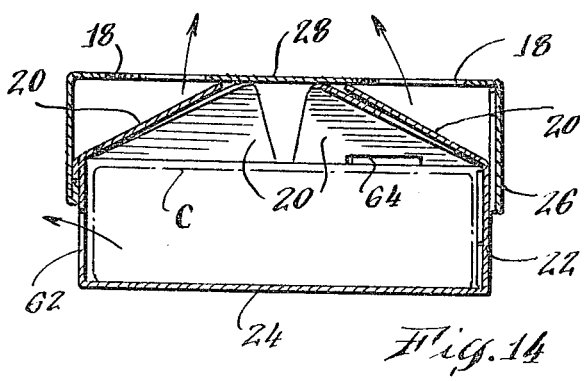

AIR FRESHENER

BACKGROUND OF THE INVENTION

1. Field of Invention

The present invention relates to cartons, and more particularly to a carton for holding an active material and controllably releasing it to the air.

2. Description of Prior Art

There are a variety of active materials for use in household and commercial applications which it is desirable to contact with and release into the ambient air. Among these are insecticides and air fresheners which can be packaged in solid form in containers having air passages which permit release. Frequently, products of this type are packaged in containers having a plurality of openings which are closed at the time of purchase but which are opened at the time of use to allow room air to circulate over the surface of a solid active material.

In one type of carton, the openings are covered with a panel of release paper. When the consumer is ready to use the product, such as an air freshener, the release paper is peeled from the face of the container to allow room air to begin circulating through the openings. In another type of carton, the consumer activates the air freshener material by squeezing to release an encapsulated active ingredient. In yet another type of carton, holes in an outer carton wall are opened or closed by a slidable inner sheet which acts as a valve.

Molded plastic containers, usually consisting of a molded shell and a separate molded cover, have been employed to hold air freshener material. However, while molded plastic containers have an aesthetically pleasing appearance, the cost of making them is higher than might be desired. The shell and cover must be molded in separate operations and stored in unassembled form until the air freshener insert is load. The cover then must be glued or otherwise secured to the shell to provide a closed container. The extra time required for the separate manufacturing and assembly operations results in added manufacturing costs for the package and ultimately for the product sold therein. The fact that the molded shells and covers must be shipped and stored in their molded form will also cause increased transportation and storage costs.

In a prior patent application, U.S. Ser. No. 25,012, filed Mar. 29, 1979, now U.S. Pat. No. 4,219,145, entitled "Carton With Adjustable Air Passages," assigned to the same assignee as the present invention, an improved package for controllably releasing active materials to the air is disclosed which has inner and outer slidable members constructed of a sheet material wherein the inner and outer members can be slidably moved between fully open and closed positions or positions intermediate thereof. The carton has a plurality of adjustable air passages and comprises: (a) a first tapered sleeve forming an outer carton unit, said first sleeve being closed at at least one end and having a plurality of spaced openings therein; and (b) a second tapered sleeve forming an inner carton unit, said second sleeve being nested within said first sleeve and being slidable between a first position and a second position, (or a position intermediate thereof) said second sleeve being closed at at least the end opposite said end closed in said first sleeve and having a plurality of spaced openings therein arranged complementally to spaced openings in said outer carton unit to align with the openings therein when said inner carton unit is in said first position, and to align with the spaces between said openings in said outer carton unit when said inner carton unit is in said second position. When opened or partially opened the active material can be released to the air.

SUMMARY OF THE INVENTION

The present invention also relates to a carton for controllably releasing active materials to the air, and more particularly, to a carton with improved, more selectable, air flow control features.

In accordance with the invention, the carton includes upper and lower, polygonally shaped, mating paperboard units which are relatively movable along a longitudinal axis of the carton.

The upper unit includes a plurality of openings through which air can flow to circulate about the surface of a solid active material disposed between the upper and lower units. This air flow diffuses the solid into the atmosphere.

The lower unit includes a plurality of resilient fingers which are normally retained beneath the openings and parallel to the top surface of the upper unit. As the upper unit is moved away from the lower unit along the axis of the carton, the resilient fingers spring upwardly selectively exposing portions of each opening enabling a controlled amount of air to flow through the carton to contact the active material. Reverse movement causes the fingers to reclose the openings.

Alternatively, the fingers lie flat, but are provided with spaces therebetween permitting air to contact the active material and diffuse it to the atmosphere. Sidewalls of the lower unit can also be provided with openings which are normally covered by the solid side walls of the upper unit, through which active material can be diffused upon selective movement of the upper and lower units along the longitudinal axis of the carton. Additionally, the fingers may also include openings in their body to aid the diffusion process.

The upper and lower units have slidably engaging sidewalls which frictionally reatin the units of the carton in axially adjusted positions relative to each other. The regular polygonal shape of each unit precludes their relative rotation, while engaging flanges on the upper and lower unit preclude their separation.

BRIEF DESCRIPTION OF THE DRAWING

Further objects and advantages of the invention will become apparent from the following description and claims, and from the accompanying drawings, wherein:

FIG. 1 is a top plan view of the blank for forming the lower unit of the carton of the present invention;

FIG. 2 is a top plan view of the blank for forming the upper unit of the carton of the present invention;

FIGS. 3 and 4 are top plan views of the blank of FIG. 1 folded in successive steps to form the lower unit of the carton of the present invention;

FIG. 5 is a cross-sectional view taken substantially along the plane indicated by line 5—5 of FIG. 3;

FIG. 6 is a cross-sectional view taken substantially along the plane indicated by line 6—6 of FIG. 4;

FIGS. 7 and 8 are top plan views of the blank of FIG. 2 folded in successive steps to form the upper unit of the carton of the present invention;

FIG. 9 is a cross-sectional view taken substantially along the plane indicated by line 9—9 of FIG. 8;

FIG. 10 is a perspective view of the assembled carton of the present invention;

FIG. 11 is a cross-sectional view taken substantially along the plane indicated by line 11—11 of FIG. 10;

FIG. 12 is a view similar to FIG. 11, but illustrating the manner of relatively separating the upper and lower units of the carton along an axis of the carton to permit diffusion of an active material to the air;

FIG. 13 is a top plan view of the carton of FIG. 12; and

FIG. 14 is a view similar to FIG. 12, but illustrating an alternate mode of operation to permit diffusion of an active material to the air.

DETAILED DESCRIPTION OF THE PREFERRED EMBODIMENT

Referring now to the drawings in detail, wherein like numerals indicate like elements throughout the several views, the carton 10 of the present invention includes an upper and lower, regular polygonally shaped, mating paperboard units 12 and 14 which are relatively movable along the longitudinal axis 16 of the carton 10.

The upper unit 12 includes a plurality of openings 18 formed in a top wall 28 through which air can flow to circulate about the surface of a solid active material C disposed within the lower unit 14. This air flow diffuses the solid C into the atmosphere. Top wall 28 is in the shape of a regular polygon, e.g., a hexagon, and includes a sidewall 26 extending downwardly from each edge of the polygonally shaped top wall.

The lower unit 14 includes a plurality of resilient, triangular-shaped fingers 20. Each finger 20 is hingedly connected to a sidewall panel 22 of lower unit 14, which in turn is hingedly connected to a polygonally shaped base 24. For purposes of illustration, the base 24 has been shown as being hexagonal in shape. Base 24 is complemental in shape to top wall 28 of upper unit 12.

As the upper unit 12 is moved away from the lower unit 14 along the axis 16 of the carton 10, the triangular-shaped resilient fingers 20 can be formed so as to spring upwardly (see, e.g., FIG. 14), selectively exposing portions of each opening 18 enabling a controlled amount of air to flow through the carton 10 to contact the active material C. Reverse movement causes the fingers 20 to pivot downwardly beneath each of the openings 18 to close the same.

Alternatively, fingers 20 can lie in a horizontal plane perpendicular to axis 16 and parallel to the top wall 28 of upper unit 12 (see, e.g., FIG. 12). Fingers 20 have spaces 60 therebetween (see FIGS. 4 and 13) permitting air which enters openings 18 to contact active material C and diffuse it to the atmosphere, as indicated by the arrows in FIG. 12. Side wall panels 22 of lower unit 14 can also be provided with openings 62 which are normally covered by the solid side walls 26 of upper unit 12, through which active material C can also be diffused upon selective movement of the upper and lower units along the longitudinal axis 16 of carton 10. Additionally, the fingers 20 may also include openings 64 in their body to aid the diffusion process.

The sidewall panels 26 on upper unit 12 are slidably engaged over corresponding sidewall panels 22 on lower unit 14. The regular polygonal shape of each unit 12 and 14 precludes their relative rotation.

The sidewall panels include means to frictionally engage each other and retain the units 12 and 14 of the carton 10 in adjusted positions relative to each other as relative movement occurs along the axis 16. Engaging flanges 30 and 32 on the sidewalls of upper and lower units 12 and 14, respectively, preclude separation of the units by engaging each other at the maximum separated position of base 24 and top wall 28, along axis 16, as shown in FIGS. 12 and 14. Because of the unsecured nature of the flanges 32, as described hereinafter, the flanges 32 are urged outwardly into frictional engagement with overlying sidewall 26 of upper unit 12 to aid retention of the upper and lower units in adjusted axial relation.

As shown in FIGS. 2 and 1, the upper and lower units 12 and 14 are formed from substantially planar paperboard blanks 40 and 50, respectively. Blank 40 in addition to the hexagonal top wall 28 containing openings 18, and the rectangular sidewall panels 26 hinged by a score line 42 to each edge of the regular polygonally-shaped top wall 28, includes a side flap 44 connected by score lines 46 to the lateral edges of every other sidewall panel 26. Accordingly, when the sidewall panels are erected by bending them 90 degrees about score lines 42, into an upright condition (see FIGS. 8 and 9), the flaps 44 are adhesively joined to an adjacent sidewall panel 26 to retain the upright configuration of the sidewalls. Flanges 30 are formed by folding a flap 30 along a score line 48, 180 degrees, and adhesively securing it to its adjacent sidewall 26, as shown in FIG. 7. Every other sidewall 26, containing the side flaps 44, contains one of the flaps 30.

The blank 50 in addition to the regular polygonally-shaped base 24 and the sidewall, rectangular panels 22 hingedly connected to each edge of base 24 by a score line 52, includes the triangular fingers 20 connected along a score line 55 to the top edge of each one of the rectangular sidewall panels 22. As with the blank 40, every other one of the sidewall panels 22 includes a side tab 54 connected by a score line 56 to the opposite edges of every other panel 22. In erecting the blank 50 into the lower unit 14, the tabs 54 are bent inwardly 90 degrees while each of the rectangular sidewall panels 22 are bent upwardly 90 degrees (FIG. 3). The tabs 54 are adhesively connected to adjacent sidewall panels 22 to maintain the lower unit in erected condition. Then the triangular fingers 20 are bent about score lines 54 so that they overly base 24 and are substantially parallel thereto (FIG. 4).

Flanges 32 are formed by cutting each flange out from every other one of the triangular resilient fingers 20 connected to every other one of the rectangular sidewalls 22 containing tabs 54 by cutting a substantially three sided portion of each finger adjacent the score line 55, but leaving the score line 55 intact. The tab 32 is then pushed outwardly from each of the resilient fingers and pivoted backwardly 180 degrees so that it will lie in the path of movement of each of the flanges 30 on upper unit 12. The formation of tab 32 leaves opening 64 in its stead. Flanges 32 are ultimately bent almost another 90 degrees by contact with overlying side walls 26 of upper unit 12, but are resiliently urged outwardly about hinge line 55 to frictionally scrape along the adjacent side wall 26 on the upper unit 12.

What is claimed as new is:

1. A carton having selectively openable openings to control the flow of air therethrough comprising:

an upper unit including a regular, polygonally-shaped top wall portion and a plurality of sidewall panels connected thereto extending downwardly substantially perpendicular from each edge of said regular, polygonally-shaped top wall portion, said top wall portion of said upper unit including a plurality of openings therethrough, and a lower unit adapted to mate with and slide relative to said upper unit along a common longitudinal axis, said lower unit including a regular, polygonally-shaped base member complemental in shape to the top wall portion of said upper unit, and a plurality of sidewall panels extending upwardly from each edge of said regular polygonally-shaped base member substantially perpendicular thereto, the sidewall panels of said upper unit overlying the sidewall panels of said lower unit, and slidable relative thereto, and a finger member extending substantially parallel to said base member connected to the upper edge of each of said sidewall panels of said lower unit in spaced relation to each other, each of said finger members being adapted to selectively close one of said openings in said upper unit by being positioned thereunderneath, and means on said upper and lower units for precluding their separation in a direction along said longitudinal axis.

2. The carton of claim 1 wherein each of said finger members are resiliently and pivotably connected to the upper edge of each of said sidewall panels of said lower unit.

3. The carton of claim 1 wherein said means for precluding separation of said upper and lower units includes a first flange connected to the lower edge of selective ones of the sidewall panels of said upper unit disposed in the same plane and path of movement of a second flange extending from the upper edge of selective ones of the sidewall panels of said lower unit.

4. The carton of claim 3 wherein said second flanges are cut from selected ones of said finger members and bent back along a hinge line between said selected finger members and top edges of said selected side wall panels to form an opening in each of said selected finger members.

5. The carton of claim 3 wherein said first flanges are adhesively secured to said selected sidewall panels of said upper unit along the lower edge thereof.

6. The carton of claim 4 wherein each of said second flanges are freely pivotable about its hinge line and in frictional sliding engagement with a sidewall panel of said upper unit.

7. The carton of claim 1 including at least one opening in at least one sidewall panel of said lower unit.

8. The carton of claim 1 wherein said top wall portion of said upper unit and the base of said lower unit is hexagonal in shape.

9. The carton of claim 1 wherein each of said finger members is triangular in shape.

10. The carton of claim 1 wherein said openings in said top wall portion of said upper unit are equally spaced about said top wall portion.

11. A paperboard blank for forming a portion of a carton comprising a regular polygonally shaped central portion, a rectangular panel hingedly connected along a longitudinal edge to each edge of said regular polygonally shaped central portion, and a triangularly shaped panel having its base hingedly connected to an opposite longitudinal edge of each of said rectangular panels, every other one of said rectangular panels having side panels hingedly connected to a lateral edge thereof, and every other one of said triangularly shaped panels having a tab defined therein by cut lines and hingedly connected to a longitudinal edge of one of said rectangular panels.

12. A paperboard blank for forming a portion of a carton comprising a regular polygonally shaped central portion, a rectangular panel hingedly connected along a longitudinal edge to each edge of said regular polygonally shaped central portion, and only every other one of said rectangular panels having side panels pivotably connected to a lateral edge thereof, and every other one of said rectangular panels having a flange pivotably connected to a longitudinal edge thereof, said flange having a lateral dimension less than the lateral dimension of said rectangular panel to which it is pivotally connected.

13. A carton comprising:

an upper unit including a regular, polygonally-shaped top wall portion and a plurality of sidewall panels connected thereto extending downwardly substantially perpendicular from each edge of said regular, polygonally-shaped top wall portion, a lower unit adapted to mate with and slide relative to said upper unit along a common longitudinal axis, said lower unit including a regular, polygonally-shaped base member complemental in shape to the top wall portion of said upper unit, and a plurality of sidewall panels extending upwardly from each edge of said regular polygonally-shaped base member substantially perpendicular thereto, the sidewall panels of said upper unit overlying the sidewall panels of said lower unit, and slidable relative thereto, and means on said upper and lower units for precluding their separation in a direction along said longitudinal axis, said means including a plurality of locking flanges hingedly coupled to one of said upper and lower units at a distal longitudinal edge of a plurality of said side walls and folded thereagainst, and a plurality of locking flanges rigidly coupled to the other of said upper and lower units for engaging the distal edge of said folded locking flanges.

14. A carton according to claim 13, wherein said upper unit further includes a plurality of openings formed in said top wall portion, and said lower unit further includes a finger member extending substantially parallel to said base member connected to the upper edge of each of said sidewall panels of said lower unit in spaced relation to each other, each of said finger members being adapted to selectively close one of said openings in said upper unit by being positioned thereunderneath.

* * * * *